United States Patent [19]
Millar

[11] Patent Number: 4,585,451
[45] Date of Patent: Apr. 29, 1986

[54] DEVICES WHICH ARE ADAPTED TO SLOWLY RELEASE CHEMICALS, SUCH AS HORMONES, DRUGS AND MINERALS

[75] Inventor: Thomas D. Millar, Hamilton, New Zealand

[73] Assignee: AHI Operations Limited, Manukau, New Zealand

[21] Appl. No.: 492,567

[22] Filed: May 9, 1983

[30] Foreign Application Priority Data

Oct. 5, 1982 [NZ] New Zealand ............. 200564

[51] Int. Cl.⁴ .................................. A61F 5/46
[52] U.S. Cl. ......................... 604/892; 128/127; 128/131
[58] Field of Search ............. 604/890–897; 128/1 R, 127, 132; 424/19–22

[56] References Cited

U.S. PATENT DOCUMENTS

| 4,012,497 | 3/1977 | Schopflin | 424/22 |
| 4,180,064 | 12/1979 | Heller et al. | 128/130 |
| 4,198,966 | 4/1980 | Kaivola | 128/130 |
| 4,246,896 | 1/1981 | Horne et al. | 128/130 |
| 4,449,980 | 5/1984 | Millar et al. | 604/890 |

FOREIGN PATENT DOCUMENTS

| 2207939 | 2/1972 | Fed. Rep. of Germany | 128/130 |
| 0036805 | 9/1981 | France | 128/130 |

OTHER PUBLICATIONS

Birth Control, Life Magazine, 9/10/65.

Primary Examiner—C. Fred Rosenbaum
Assistant Examiner—Sherri E. Vinyard
Attorney, Agent, or Firm—Holman & Stern

[57] ABSTRACT

A device for the slow release of chemicals into the body of an animal when the device is positioned in a body cavity of that animal, is formed as a flexible core member (1) from polypropylene, polyethylene or other polymer in a shape having a plurality of lobes (4,8) one (4) of which is longer than other shorter lobes (8) and the shorter lobes (8) being foldable for insertion and removal purposes. The core (1) has a solid (3) secured to the surface thereof or forming a part of the surface thereof which solid of silicone rubber or ethylene vinyl acetate or other suitable polymer is impregnated with one or more chemicals which in use are leached therefrom by body fluids. A withdrawal ligament (14) is attached to the free end of the longer lobe.

3 Claims, 4 Drawing Figures

DEVICES WHICH ARE ADAPTED TO SLOWLY RELEASE CHEMICALS, SUCH AS HORMONES, DRUGS AND MINERALS

This invention relates to devices which are adapted to slowly release chemicals, such as hormones, drugs and minerals, and relates particularly but not exclusively to devices which are suitable for use in the body cavities of animals including vaginal cavities.

It is an object of the present invention to provide a device adapted to slowly release chemicals such as hormones, drugs and minerals and/or methods of making such devices which will at least provide the public with a useful choice.

Accordingly in one aspect the invention consists in a device for insertion into a body cavity of an animal and for producing a controlled rate of release of chemicals into the body of the animal, said device comprising a flexible member having a plurality of compressible lobes and at least some selected lobes are foldable and at least some of which have secured to the surface thereof or forming a part of the surface thereof an impregnated solid impregnated with one or more chemical impregnant which are adpated to leach therefrom when exposed to body fluids.

In a further aspect the invention consists in a method of forming a device according to the preceding paragraph, said method comprising the steps of moulding a resilient member, forming a curable mixture of two liquid silicone elastomers, incorporating a chemical impregnant in said liquid mixture of elastomers and moulding and curing said elastomer mixture in, around or in contact with said resilient member.

In many situations the physiology or pharmacology of an animal process is well enough understood that it can be manipulated by active ingredients such as hormones, drugs and minerals, but the exploitation is limited by the lack of practical methods of administering the active ingredients.

For example, oestrus synchronisation by progestogens in sheep and cattle has been known for more than 30 years but neither injection or feeding sheep or cows is a practical procedure especially under pastoral conditions.

As well as the practical difficulties involved in the administration of drugs, the question of residues is becoming increasingly important. In many cases it is unacceptable to the Authorities, such as the Animal Remedies Board to have animals injected with drugs. The question of possible residues of substances after injection is an increasing concern to such Authorities. This concern may be amplified by restrictions imposed overseas by the U.S. Federal Drug Administration and its E.E.C. equivalents. An outstanding example of this is the banning of stilboestrol in the U.S. despite the fact that carcass residues have never been demonstrated. More recently attempts have been made to overcome this residue fear by using intra-vaginal devices which are manufactured in such a way that they only slowly release chemicals over an extended period of time. U.S. Pat. Nos. 3,625,214 and 3,892,238 show typical examples of the prior art in this field. Thus the level of chemical in the blood stream of the animal being treated is kept quite low in comparison with the peak levels associated with injected materials, and the potential problem on contamination of the animal's carcass is minimised. Whilst such intra-vaginal devices have been tested and found to give satisfactory performances, all the devices of which the applicant has become aware are considered to be too expensive for large scale use.

According to the present invention, applicants have designed a device for controlled or slow chemical release which comprises a resilient member composed of or having secured thereto a solid impregnated with one or more chemicals which are adapted to leach therefrom when exposed to bodily fluids of animals. The chemicals incorporated in the solid are chemically different from the solid itself.

The chemically impregnated solid portion may comprise a silicone rubber which has been formed from a heat curable liquid silicone and which has dispersed or dissolved therein said chemical or chemicals prior to curing to form said solid.

The resilient member may itself comprise said impregnated solid, or alternatively may consist of a separate member formed of a different material. In a preferred construction the resilient member may comprise a unit of moulded resilient plastics material having a plurality of lobes, which are wholly or partially covered with impregnated skin. In its unstressed configuration the device is preferably substantially flat in order to facilitate automatic high speed moulding and handling one abutting the other. To insert the device into an animal, the lobes may be folded or compressed to reduce its external diameter, and insert into the animals vagina, or other body cavity e.g. rumen. The lobes then resiliently spring back to their original configuration to prevent the device from falling out of the cavity accidentally.

Applicants have found that an impregnated solid comprising an EVA (Ethylene Vinyl Acetate) or a cured silicone rubber is particularly suitable for allowing gradual leaching of impregnated materials. A typical silicone rubber formed from a high speed curing two part mixture of silicone elastomers of the type described in U.S. Pat. No. 3,445,420 in the name of Dow Corning Corporation is one of several which have been proved sutiable for the performance of the invention.

Preferably said two component silicone rubber is curable in two to ninety, more preferably ten to thirty seconds, at 95° to 260° C. more preferably 175° to 205° C. in typical or suitable cross sections.

Said two component silicone rubber suitably has any one or more of the following properties.

| | |
|---|---|
| (A) At Room Temperature Prior to Moulding | |
| Viscosity CPS | 300,000 to 1,800,000 |
| More preferably | 900,000 to 1,300,000 |
| Specific gravity | 1.15 to 1.35 |
| More preferably | 1.22 to 1.26 |
| (B) After Moulding with a Cure Time of 5 Min. at 350° C. | |
| Hardness, Shore A, Durometer | 30 to 65 |
| More preferably | 40 to 55 |
| Tensile Strength PSI | 50 to 3,000 |
| More preferably | 500 to 1,000 |
| Elongation % | 100 to 2,000 |
| More preferably | 400 to 600 |

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The present invention will now be described with reference to the accompanying drawings in which.

Figure 2:
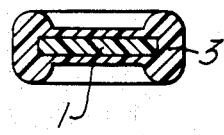
FIG. 2 is a cross section on the line II—II FIG. 1.
Figure 1:
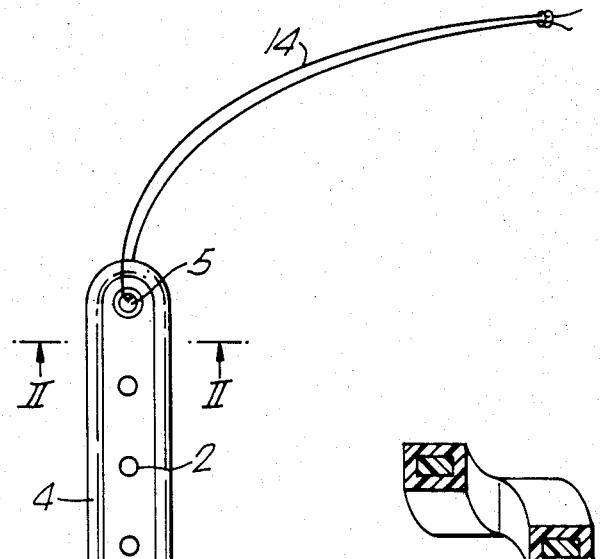
FIG. 1 is a spread out view of an unfolded device according to the invention.
Figure 4:
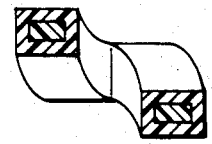
FIG. 4 is a section on the line IV—IV FIG. 3.
Figure 3:
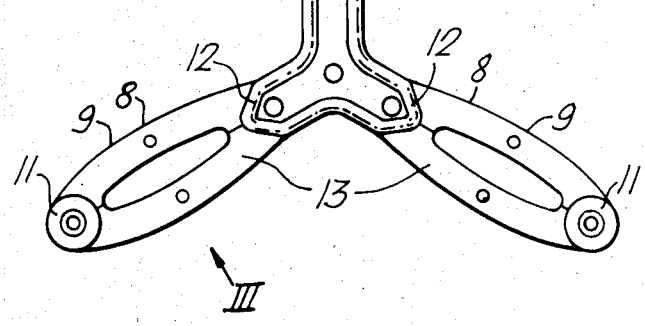
FIG. 3 is a view in the direction of arrow III FIG. 1.
Figure 3:
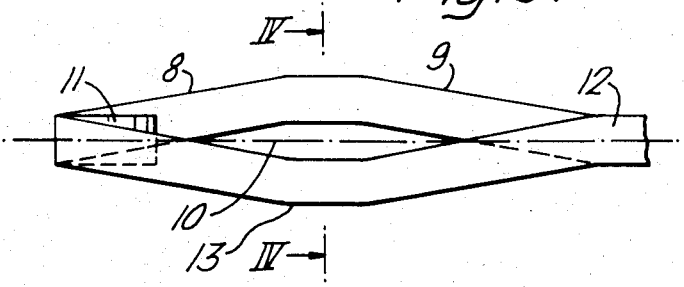

Referring to the drawings, in the preferred form of the invention shown in FIG. 1, a body 1 is moulded with a plurality of arms or lobes for example between 3 and 7 from a suitable plastics material such as polypropylene, polyethylene or ethylene vinyl acetate which are non-toxic and resiliently flexible materials. One or more of the lobes is perforated with a network of holes 2 so that a coating or skin preferably a polymer coating 3 containing chemical impregnants in the form of drugs, trace elements or minerals for example, may be moulded around at least the free ends of the lobes of the body 1 so that the chemical ingredient is provided in the skin while the lobes form the skeleton of the device. Because the chemical ingredient is in the skin, it is available on the surface thereof for its pharmaceutical or other properties. One of the lobes 4 is longer than the others and at the outer end of the lobe 4 is a hole 5 through which may be threaded a withdrawing ligament which may be moulded as a separate unit with a "T" shaped head or alternatively the ligament may be moulded in one piece with body 1 to substantially eliminate post moulding assembly costs.

We have however found as a result of an extensive programme of application and removal of the devices, that the simplest and most effective method of effecting removal is to have the ligament 14 (which may be mono filament or multi-filament cord) looped through the hole 5 in one lobe of the device to provide withdrawal action by pulling on that one lobe only. When this one lobe is pulled, the other two lobes will fold over and trail behind as the device is withdrawn from the animal. This folding action is assisted by the looped and non-planar construction of the other two lobes. This has been proved to give most reliable withdrawl with the least possible risk of discomfort or damage to the animal.

Any of the lobes, but preferably the remaining lobes 8 are provided as loops with one arm 9 of each loop displaced in one direction from the plane 10 containing the ends 11 and 12 of the loop and the other arm 13 displaced in the opposite direction from the plane 10.

We have also found that the application, retention and removal of the device may be facilitated when the arm on which the withdrawal filament is attached is longer by upwards of 25% for example longer by 50% than each of the other (two) arms when a total of three arms is included.

After moulding of the body or skeleton 1 in the suitable non-toxic and flexible material, the skeleton 1 is transferred to another mould in which the polymer substance 3 is moulded. Such a substance is, for example an EVA or a more rapid curing two component liquid silicone rubber which is moulded around each of the lobes 1. A typical rubber which is generally described in U.S. Pat. No. 3,445,420 is available commercially and has curing times which vary from one month at ambient temperature to five seconds at 200° C. By using an appropriate temperature e.g. one approaching 200° C., these silicone rubbers can be cured very rapidly. During moulding of silicone rubber the two components of the silicone rubber are introduced into the moulding machine just prior to injection. The active ingredient whether it be a progestogen or oestrogen or other substance is premixed with one or both of the silicone rubber components or alternatively may be dosed automatically as the two silicone rubber components are fed into the mould of the moulding machine.

The foregoing describes an intra-vaginal (but which may be used in other animal cavities) device of particular configuration but other physical configurations are possible with the device which is characterised by being simply and cheaply produced by normal moulding such as injection moulding in a single stage from one material or in two stages, firstly by moulding a skeleton or carrier and secondly by coating that carrier as required with a suitable substance e.g. a polymer which acts as a drug release polymer coating. We have found that a two part high speed curing silicone rubber is a useful substance in this regard.

The surfaces of the skin may be extended by indentations, undulations and/or apertures so that the surface area exposed to body fluids is increased. Such undulations or indentations may have a smooth profile so they do not unnecessarily collect or harbour bacteria or collections of bodily substances and/or damage animal tissue. The formation of some or all of the lobes as loops increases the surface area.

A central orifice may be provided in the carrier moulding to allow for draining or flow of bodily fluids and/or withdrawal of the device by means of a suitably attached cord should this be preferred to the arrangements above described.

The insertion of the device may be effected by folding the lobes into a closed position and by use of an applicator comprising, for example, a hollow handled shaft having a longitudinal slot, the long lobe and the ligament being inserted in the shaft with the ligament extending out through the slot and the other lobes being folded back over the outside of the shaft. After insertion the natural elasticity of the lobes will cause these to open against the internal surfaces of the vagina or other body cavity to retain the device in said position securely and with minimal discomfort to the animal.

While the incorporation of drugs in a polymer device and its removal at the end of a treatment period does not completely eliminate the problems of residues, it is more acceptable to many approving Authorities and they will consider a procedure such as induction of lactation, by an administration of oestrogens via a polymer device where injections of oestrogens are completely unacceptable.

In addition, sustained release of drugs has many other advantages. The amount of drug (or other substances) required to achieve a desired effect is often substantially reduced compared with injection or ingestion. Where substances are ingested the uptake by the gut and the metabolism of the entero-hepatic circulation offer substantial barriers to the effectiveness of materials reaching the target site.

Also, the passage of material through the gut is essentially a limiting factor to the effective time of oral does of a substance. With both injections and oral dosing, the material is usually in a soluble form and reaches high concentrations both at the site of administration and in the blood. This can cause complications both through local toxicity and in other parts of the body. As the clearance of a material is proportional to its concentration this means that usually a large amount of injected material is wasted when sufficient is injected to act over a 24 hour period because of the high clearance at the time of such blood levels. With sustained release, the blood level of material can be maintained at much closer to the effective level. This frequently means that as well as reducing or avoiding toxicity problems, the amount of administered material is substantially reduced often by a factor of 100 or more.

The release of drugs from polymers has a wide variety of applications to animal production in New Zealand and in other countries. Many drug carrying devices have been devised and their descriptions published.

These have all suffered from limitations either in their effectiveness in use, damage or discomfort to the animal and/or the cost effectivenss and/or high labour cost of production.

Devices have been described for assistance in synchronisation of oestrus in sheep and cattle, for induced lactation in cattle, for induced calving etc.

Testosterone treatment of cows induces them to perform male mounting behaviour, so assisting in the detection of animals which are ready for mating.

It is possible to stimulate lactation by the administratiion of growth hormones; and many other possibilities exist for the application to animals of various minerals and drugs for a number of reasons.

For example one or more mineral trace elements in addition to or instead of a hormonal or oestrogenic or anthelmintic ingredient may be incorporated in the skin during manufacture thereof. In such cases the skin may be of ethylene vinyl acetate or polymer and may be integral with the body or skeleton of the device.

The body or skeleton acts as a mechanical framework or support and the skin is an outer covering of sufficient thickness so that in use the skin erodes away freeing the active ingredient over a satisfactory period of time, the active ingredient being leached out by action of the animal's body fluids.

Whilst the foregoing description is particularly directed to intra-vaginal applications, it is possible that devices according to the invention could be used in other parts of the anatomy of animals as well.

We have found that the preferred shape also has the advantage of reducing the incidence of accidental expulsion.

I claim:

1. A device for insertion into the vaginal cavity of an animal and for producing a controlled rate of release of chemicals into said vaginal cavity, said device comprising a flexible member having a plurality of compressible lobes wherein one lobe is longer than the others and the shorter lobes are each in the form of a closed loop, wherein each loop is formed by two arms joined together such that each loop has two ends and the central portion of each arm is displaced away from a plane containing both ends of the loop and in opposite directions, and wherein said shorter lobes are foldable during insertion of said device into and removal of said device from the vaginal cavity and at least some of the lobes having on a surface thereof a solid impregnated with chemical impreganat adapted to leach from the solid when exposed to body fluids, said longer lobe having drawstring means for a single step withdrawal of said device from the body cavity.

2. The device of claim 1 wherein the longer lobe is greater than 25% longer than the shorter lobes.

3. The device of claim 2 wherein the longer lobe is greater than 50% longer than the shorter lobes.

* * * * *